(12) United States Patent
Itkowitz et al.

(10) Patent No.: US 12,702,278 B2
(45) Date of Patent: Aug. 11, 2026

(54) TECHNIQUES FOR CONTROLLING AN IMAGING DEVICE

(71) Applicant: INTUITIVE SURGICAL OPERATIONS, INC., Sunnyvale, CA (US)

(72) Inventors: Brandon D. Itkowitz, San Jose, CA (US); Yiming Mei, Fremont, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/953,511

(22) Filed: Nov. 20, 2024

(65) Prior Publication Data

US 2025/0082184 A1 Mar. 13, 2025

Related U.S. Application Data

(63) Continuation of application No. 17/599,989, filed as application No. PCT/US2020/026469 on Apr. 2, 2020, now Pat. No. 12,178,399.

(Continued)

(51) Int. Cl.
*A61B 34/20* (2016.01)
*A61B 1/00* (2006.01)
(Continued)

(52) U.S. Cl.
CPC ...... *A61B 1/00149* (2013.01); *A61B 1/00006* (2013.01); *A61B 1/00009* (2013.01);
(Continued)

(58) Field of Classification Search
None
See application file for complete search history.

(56) References Cited

U.S. PATENT DOCUMENTS

2005/0187432 A1 8/2005 Hale et al.
2006/0291657 A1 12/2006 Benson et al.
(Continued)

FOREIGN PATENT DOCUMENTS

CN 103728868 A 4/2014
EP 0054128 A2 6/1982
(Continued)

OTHER PUBLICATIONS

Dong H., et al., “Workspace Density and Inverse Kinematics for Planar Serial Revolute Manipulators,” Mechanism and Machine Theory, 2013, vol. 70, pp. 508-522.

(Continued)

*Primary Examiner* — Eileen M Adams
(74) *Attorney, Agent, or Firm* — Artegis Law Group, LLP

(57) ABSTRACT

Techniques for controlling an imaging device include a first repositionable arm comprising a plurality of actuators configured to cause movement of the first repositionable arm and a plurality of joints; and a controller comprising one or more hardware processors. The controller is configured to determine whether an imaging device supported by the first repositionable arm comprises an articulable joint coupling an imaging apparatus to a shaft of the imaging device; in response to a determination that the imaging device comprises the articulable joint: command the plurality of actuators to move the plurality of joints and the articulable joint to position and orient a field of view of the imaging apparatus; and in response to a determination that the imaging device does not comprises the articulable joint: command the plurality of actuators to move the plurality of joints to position and orient the field of view of the imaging apparatus.

20 Claims, 8 Drawing Sheets

Related U.S. Application Data

(60) Provisional application No. 62/828,825, filed on Apr. 3, 2019.

(51) Int. Cl.
*G06T 7/70* (2017.01)
*H04N 23/695* (2023.01)
*H04N 23/50* (2023.01)

(52) U.S. Cl.
CPC .......... *A61B 1/00183* (2013.01); *A61B 34/20* (2016.02); *G06T 7/70* (2017.01); *H04N 23/695* (2023.01); *A61B 2034/2057* (2016.02); *G06T 2207/10068* (2013.01); *H04N 23/555* (2023.01)

(56) References Cited

U.S. PATENT DOCUMENTS

| | | | | |
|---|---|---|---|---|
| 2008/0122958 | A1* | 5/2008 | Huseth | G08B 13/19689 348/E7.086 |
| 2016/0174930 | A1 | 6/2016 | Braun et al. | |
| 2016/0302875 | A1 | 10/2016 | Hourtash | |
| 2016/0309992 | A1 | 10/2016 | Stith et al. | |
| 2016/0360188 | A1 | 12/2016 | Kim et al. | |
| 2017/0000574 | A1* | 1/2017 | Itkowitz | A61B 1/0016 |
| 2017/0105713 | A1 | 4/2017 | Frimer et al. | |
| 2017/0305016 | A1* | 10/2017 | Larkin | A61B 1/0051 |
| 2017/0333141 | A1 | 11/2017 | Itkowitz et al. | |
| 2019/0102881 | A1* | 4/2019 | Fujimoto | H04N 23/55 |
| 2022/0142721 | A1 | 5/2022 | Itkowitz et al. | |

FOREIGN PATENT DOCUMENTS

| | | | |
|---|---|---|---|
| EP | 3115159 | A1 | 1/2017 |
| WO | WO-2016069648 | A1 | 5/2016 |
| WO | WO-2016126914 | A1 | 8/2016 |

OTHER PUBLICATIONS

Extended European Search Report for Application No. EP22199144.1, mailed on Jan. 12, 2023, 09 pages.
International Search Report and Written Opinion for Application No. PCT/US2020/026469, mailed Jul. 28, 2020, 12 pages.
International Preliminary Report on Patentability for Application No. PCT/US2020/026469 mailed on Oct. 14, 2021, 7 pages.
Vertut, J., and Coiffet, P., “Robot Technology: Teleoperation and Robotics Evolution and Development,” English translation, Prentice-Hall, Inc., Inglewood Cliffs, NJ, USA 1986, vol. 3A, 332 pages.

* cited by examiner

500

510 Determine a direction of view based on imaging device information

520 Determine a view up direction based on imaging device information

530 Determine a depth of a point of interest from the imaging device

540 Determine a position of a center of view of the imaging device

TECHNIQUES FOR CONTROLLING AN IMAGING DEVICE

RELATED APPLICATIONS

This application is a continuation of U.S. patent application Ser. No. 17/599,989, titled "System and Method of View Restoration" and filed on Sep. 29, 2021, which is a U.S. National Stage patent application of International Patent Application No. PCT/US2020/026469, filed Apr. 2, 2020, which claims the benefit of U.S. Provisional Patent Application No. 62/828,825, filed on Apr. 3, 2019. The subject matter of these related applications is hereby incorporated herein by reference.

TECHNICAL FIELD

The present disclosure relates generally to control of devices with repositionable arms for controlling an imaging device and more particularly to restoring a view of the imaging device when the imaging device is moved between repositionable arms and/or workspace ports.

BACKGROUND

More and more devices are being replaced with autonomous and semiautonomous electronic devices. This is especially true in industrial, entertainment, educational, and other settings. As a medical example, the hospitals of today with large arrays of autonomous and semiautonomous electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These electronic devices provide both advantages and challenges to the personnel operating them. Many of these electronic devices may be capable of autonomous or semi-autonomous motion of one or more repositionable arms and/or instruments. For example, in order to facilitate flexible use of the electronic devices, the electronic devices may be configured to have an imaging device that can be moved between (e.g., mounted to) different repositionable arms and/or moved between different ports used to access a workspace. However, when the imaging device is moved between the different repositionable arms and/or different workspace ports, the image captured by the imaging device is likely to change. In some embodiments, this may reduce a usability of the images from the imaging device and/or cause delays in further performing a procedure that utilizes the images from the imaging device.

Accordingly, improved methods and systems for restoring the view of the imaging device after the imaging device is moved between the different repositionable arms and/or the different workspace ports are desirable.

SUMMARY

Consistent with some embodiments, a computer-assisted device includes an imaging device and a controller coupled to the imaging device. The controller is configured to record kinematic information, imaging information, or both the kinematic information and the imaging information of the computer-assisted device before movement of the imaging device from a first repositionable arm to a second repositionable arm or from a first workspace port to a second workspace port; detect the movement of the imaging device from the first repositionable arm to the second repositionable arm or from the first workspace port to the second workspace port; determine, in response to the detection, a desired position and orientation of the imaging device based on the recorded kinematic information, the recorded imaging information, or both the recorded kinematic information and the recorded imaging information; and move the imaging device based on the desired position and orientation.

Consistent with some embodiments, a method includes recording, using a controller, kinematic information, imaging information, or both the kinematic information and the imaging information of a computer-assisted device before movement of an imaging device from a first repositionable arm to a second repositionable arm or from a first workspace port to a second workspace port; detecting, by the controller, the movement of the imaging device from the first repositionable arm to the second repositionable arm or from the first workspace port to the second workspace port; determining, by the controller in response to the detecting, a desired position and orientation of the imaging device based on the recorded kinematic information, the recorded imaging information, or both the recorded kinematic information and the recorded imaging information; and moving, by the controller, the imaging device based on the desired position and orientation.

Consistent with some embodiments, a non-transitory machine-readable medium comprising a plurality of machine-readable instructions which when executed by one or more processors associated with a computer-assisted device are adapted to cause the one or more processors to perform any of the methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

Figure 1:
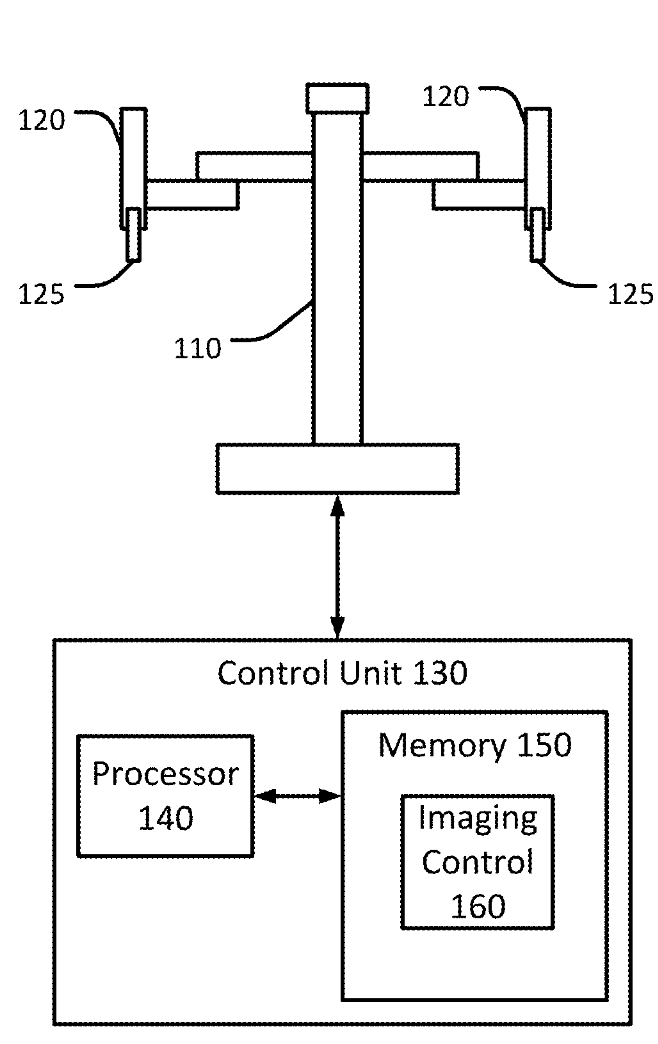
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like-may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of the devices and elements in terms of their state in three-dimensional space. As used herein, the term "position" refers to the translational placement of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, and for a device with repositionable arms, the term "proximal" refers to toward the base of the device and "distal" refers to away from the base.

Aspects of the invention are described primarily in terms of an implementation using a computer-aided medical system such as a da Vinci® Surgical System commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on any surgical systems such as the da Vinci® Surgical Systems are merely exemplary and are not to be considered as limiting the scope of the inventive aspects disclosed herein. For example, any reference to surgical instruments and surgical methods is non-limiting as the instruments, systems, and methods described herein may be used for animals, human cadavers, animal cadavers, portions of human or animal anatomy, tissue removed from human or animal anatomies (with or without return to a human or animal anatomy), non-surgical diagnosis, industrial systems, and general robotic or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a computer-assisted device 110 with one or more repositionable arms 120. Each of the one or more repositionable arms 120 may support one or more instruments 125. In some examples, computer-assisted device 110 may be consistent with a computer-assisted medical device such as a computer-assisted non-invasive diagnosis device and/or a computer-assisted surgical device. The one or more instruments 125 may include instruments, imaging devices, and/or the like. In some medical examples, the instruments may include medical instruments, such as clamps, grippers, retractors, cautery instruments, suction instruments, suturing devices, and/or the like. In some medical examples, the imaging devices may include endoscopes, cameras, ultrasonic devices, fluoroscopic devices, and/or the like.

Computer-assisted device 110 is coupled to a control unit 130 via an interface. The interface may include one or more cables, connectors, and/or buses and may further include one or more networks with one or more network switching and/or routing devices. Control unit 130 includes a processor 140 coupled to memory 150. Operation of control unit 130 is controlled by processor 140. And although control unit 130 is shown with only one processor 140, it is understood that processor 140 may be representative of one or more central processing units, multi-core processors, microprocessors, microcontrollers, digital signal processors, field programmable gate arrays (FPGAs), application specific integrated circuits (ASICs), graphics processing units (GPUs) and/or the like in control unit 130. Control unit 130 may be implemented as a stand-alone subsystem and/or as a board added to a computing device or as a virtual machine.

Memory 150 may be used to store software executed by control unit 130 and/or one or more data structures used during operation of control unit 130. Memory 150 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

In some embodiments, computer-assisted system 100 may be found in a medical setting such as an operating room and/or an interventional suite. And although computer-assisted system 100 includes only one computer-assisted device 110 with two repositionable arms 120, one of ordinary skill would understand that computer-assisted system 100 may include any number of computer-assisted devices with repositionable arms and/or instruments of similar and/or different design from computer-assisted device 110. And although computer-assisted device 110 is shown as a stand-alone unit (e.g., with a base on the floor), computer-assisted device 110 may be wall-mounted, ceiling mounted, mounted to a table and/or workspace, and/or the like. In some examples, each of the computer-assisted devices may include fewer or more repositionable arms 120 and/or instruments 125.

An imaging control module 160 may support autonomous and/or semiautonomous control of computer-assisted device 110. Imaging control module 160 may additionally include one or more application programming interfaces (APIs) for receiving position, motion, and/or other sensor information from computer-assisted device 110, exchanging position, motion, and/or collision avoidance information with other control units regarding other devices, and/or planning and/or assisting in the planning of motion for computer-assisted device 110, repositionable arms 120, instruments 125, and/or the like. In addition, imaging control module 160 may provide commands to one or more actuators used to control positions and/or orientations of repositionable arms 120, instruments 125, and/or the like. And although imaging control module 160 is depicted as a software module, imaging control module 160 may be implemented using hardware, software, and/or a combination of hardware and software.

One of the tasks of imaging control module 160 is to help support the movement of an imaging device from a first one of the repositionable arms 120 to a second one of the repositionable arms 120, which is sometimes referred to as an arm swap. In some examples, the imaging device may be one of the instruments 125. Another of the tasks of imaging control module 160 is to help support the movement of the imaging device between different ports (with or without an arm swap) used to access a workspace, which is sometimes referred to as a port hop. In some examples, these tasks of imaging control module 160 include determining relevant aspects of a view of the imaging device before the arm swap and/or port hop and then moving the imaging device after the arm swap and/or port hop so as to minimize differences between the view of the imaging device after the arm swap and/or port hop and the view of the imaging device before the arm swap and/or port hop.

Figure 2:
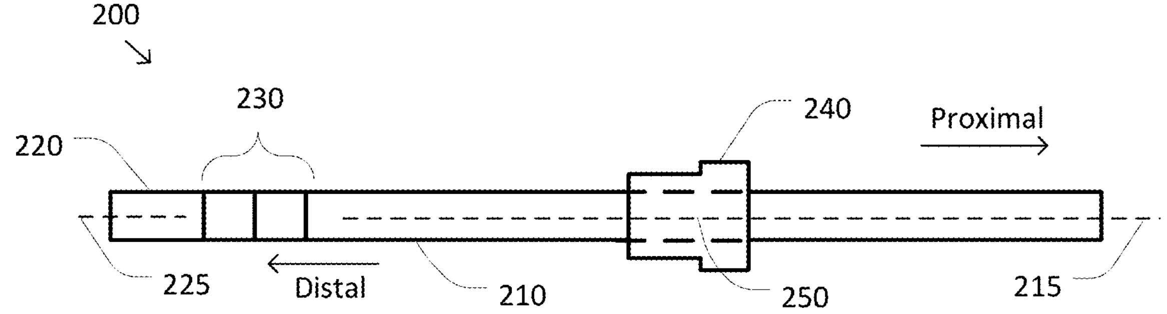
FIG. 2 is a simplified diagram of an imaging device introduced into a workspace according to some embodiments.

FIG. 2 is a simplified diagram of an imaging device 200 introduced into a workspace according to some embodiments. In some examples, imaging device 200 may be one of the one or more instruments 125. As shown in FIG. 2, imaging device includes an elongated shaft 210 extending from a proximal end where it is mounted to a repositionable arm (e.g., one of the repositionable arms 120) and a distal end where an imaging apparatus is located. In some examples, imaging apparatus 220 is oriented so that the direction of view by which it obtains images is oriented to point distal to a longitudinal axis 225 of imaging apparatus 220. In some examples, imaging apparatus 220 may correspond to a camera, an endoscope, a stereoscopic endoscope, and/or the like. And although imaging device 200 is shown with a straight shaft 210, imaging devices with an angled shaft are also possible. In some examples, the angled shaft may include a bend so that the direction of view and axis 225 of imaging apparatus 220 are at angle relative to a longitudinal axis 215 of shaft 210. In some examples, the angle of the bend may be between 0 and 45 degrees.

According to some embodiments, imaging device 200 may optionally include an articulated wrist 230, which may be used to dynamically adjust an angle between the direction of view of imaging apparatus 220 and longitudinal axis 215 of shaft 210. In some examples, articulated wrist 230 may allow articulation of the direction view in one or more degrees of freedom relative to longitudinal axis 215 of shaft 210. In some examples, the one or more degrees of freedom may include a pitch and/or a yaw degree of freedom.

According to some embodiments, imaging device 200 may be introduced into a workspace (e.g., an interior anatomy of a patient in a medical example) by inserting imaging device 200 through a port 240. In some examples, port 240 may be a cannula, a trocar, and/or the like. In some examples, port 240 is typically located at a periphery of the workspace. In some examples, the periphery may correspond to a boundary of a pressure vessel, an isolation chamber, and/or the like. In some medical examples, the periphery may correspond to a dermal layer of an anatomy. In some examples, to avoid placing stress on imaging device 200, port 240, and/or the periphery, the repositionable arm to which imaging device 200 is mounted may have its motion constrained so that shaft 210 is only rotated about a remote center of motion 250 and/or shaft 210 is inserted and/or retracted along longitudinal axis 215. In some examples, remote center of motion 250 may be centered about the point where port 240 allows shaft 210 to pass through the periphery. In some examples, the rotations about remote center of motion 250 may include one or more rotational degrees of freedom. In some examples, the one or rotational degrees of freedom may be one or more of a pitch rotation about remote center of motion 250, a yaw rotation about remote center of motion 250, and/or a roll rotation about remote center of motion 250 and longitudinal axis 215.

Figure 3:
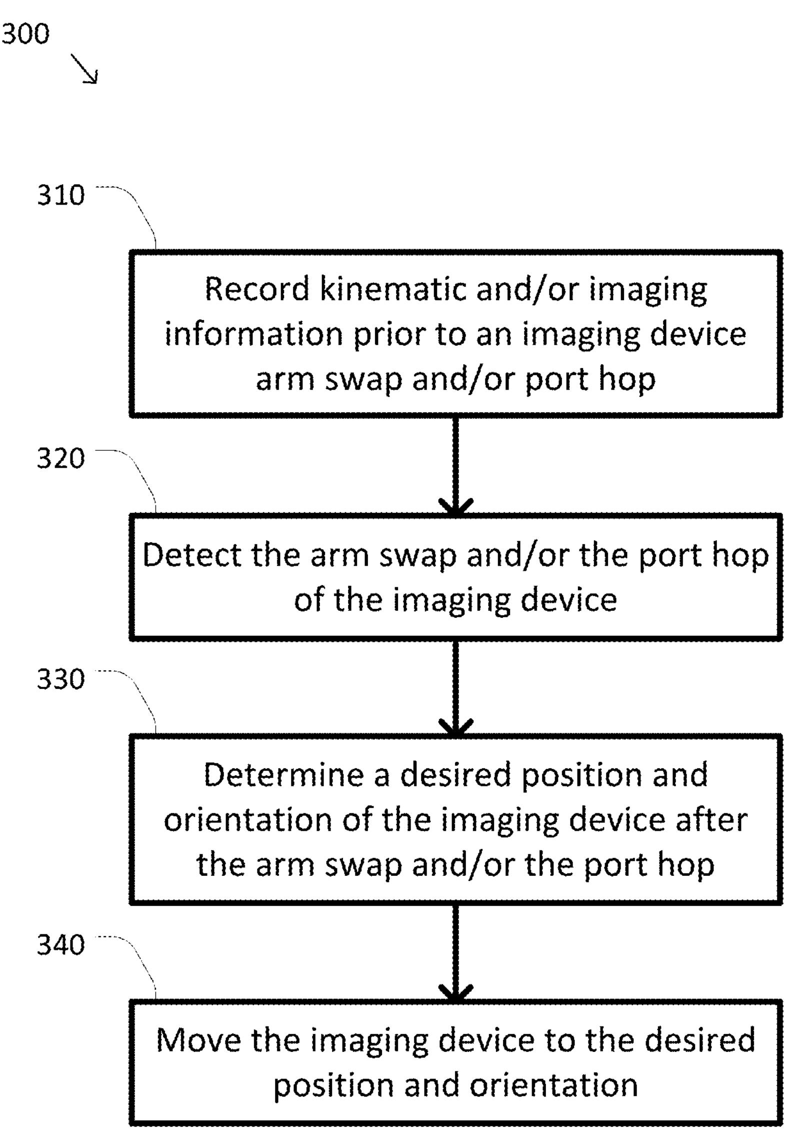
FIG. 3 is simplified diagram of a method of view restoration according to some embodiments.

FIG. 3 is simplified diagram of a method of view restoration according to some embodiments. One or more of the processes 310-340 of method 300 may be implemented, at least in part, in the form of executable code stored on non-transitory, tangible, machine-readable media that when run by one or more processors (e.g., the processor 140 in control unit 130) may cause the one or more processors to perform one or more of the processes 310-340. In some embodiments, portions of method 300 may be performed by a module, such as imaging control module 160. In some embodiments, method 300 may be used to restore the view of an imaging device (e.g., imaging device 200) after the imaging device is moved between/arm swapped repositionable arms (e.g., repositionable arms 120) and/or between workspace ports/port hopped (e.g., between ports 240). Aspects of method 300 are described with respect to the examples of FIGS. 4A and 4B.

Figure 4A:
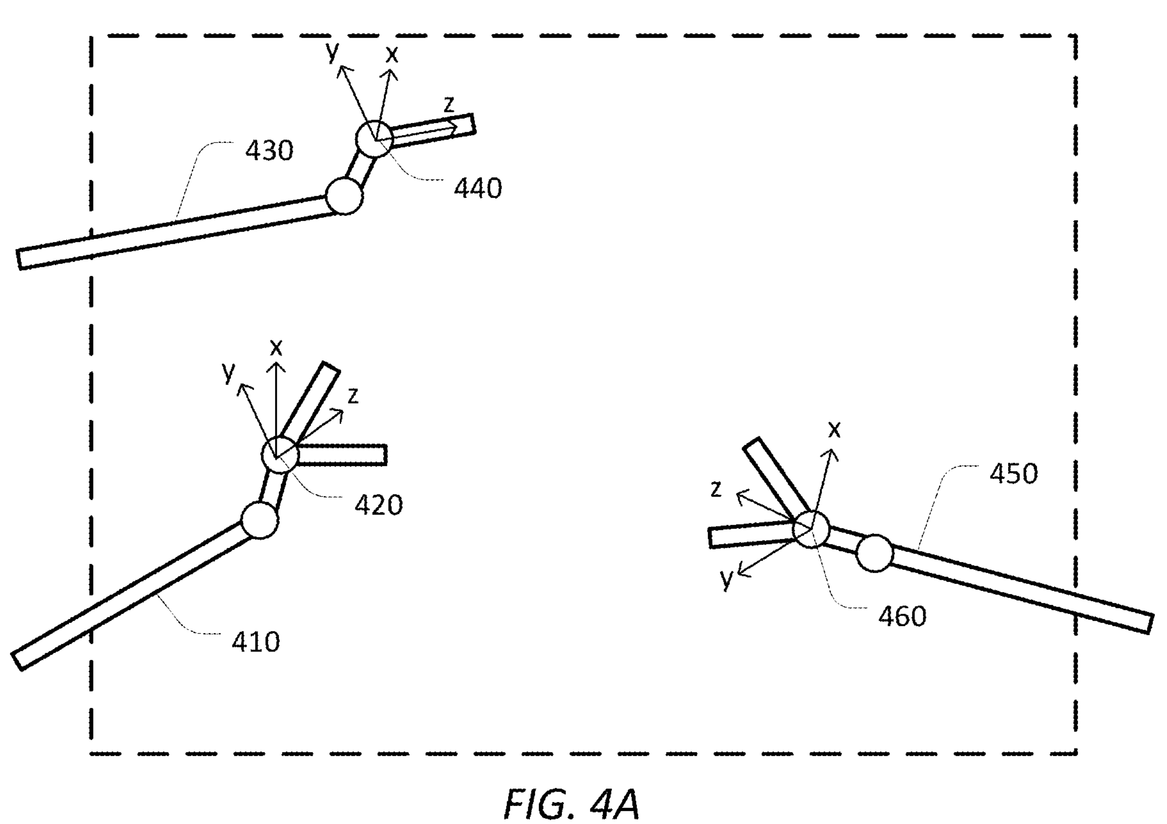
FIG. 4A is a simplified diagram of a view of an imaging device before an arm swap and/or port hop according to some embodiments.

FIG. 4A is a simplified diagram of a view of an imaging device before an arm swap and/or port hop according to some embodiments. As shown in FIG. 4A, the view of the imaging device, which roughly corresponds to the dashed rectangle, shows that the view includes three instruments. And although three representative instruments are shown in FIG. 4A, other instruments with other positions, orientations, and/or configurations are also possible. Additionally, even though the three instruments are depicted as being fully visible in FIG. 4A, some or all of each of the instruments may be occluded by each other, objects in the workspace (e.g., anatomy), and/or the like.

An instrument 410 extends into the view from the lower left. As shown, instrument 410 includes an articulated wrist and an end effector with gripping jaws. A position of instrument 410 and its end effector may be described using a position of coordinate frame 420 and an orientation of the end effector may be described using orientations of the x, y, and z axes of coordinate frame 420. In some examples, the position and orientation of coordinate frame 420 may be mapped by determining a relative transform of coordinate frame 420 relative to the imaging device using one or more kinematic models of instrument 410 and a repositionable arm to which instrument 410 is mounted as shown in Equation 1, where FK corresponds to the forward kinematics of the indicated devuce.

$$T_{instrument} = FK(\text{instrument}) \quad \text{Equation 1}$$

-continued $$T_{imagingdevice} = FK(\text{imaging device})$$

$$T_{instrument\ wrt\ imaging\ device} = T_{imagingdevice}^{-1} * T_{instrument}$$

An instrument 430 extends into the view from the left. As shown, instrument 430 includes an articulated wrist and an end effector. A position of instrument 430 and its end effector may be described using a position of coordinate frame 440 and an orientation of the end effector may be described using orientations of the x, y, and z axes of coordinate frame 440. In some examples, the position and orientation of coordinate frame 440 may be mapped to the world coordinate frame using an inverse of one or more kinematic models of instrument 430 and a repositionable arm to which instrument 430 is mounted. In some examples, the position and orientation of coordinate frame 440 may be additionally mapped to the viewing coordinate frame of the imaging device using one or more kinematic models of the imaging device and a repositionable arm to which the imaging device is mounted.

An instrument 450 extends into the view from the lower right. As shown, instrument 450 includes an articulated wrist and an end effector with gripping jaws. A position of instrument 450 and its end effector may be described using a position of coordinate frame 460 and an orientation of the end effector may be described using orientations of the x, y, and z axes of coordinate frame 460. In some examples, the position and orientation of coordinate frame 460 may be mapped to the world coordinate frame using an inverse of one or more kinematic models of instrument 450 and a repositionable arm to which instrument 450 is mounted. In some examples, the position and orientation of coordinate frame 460 may be additionally mapped to the viewing coordinate frame of the imaging device using one or more kinematic models of the imaging device and a repositionable arm to which the imaging device is mounted.

Figure 4B:
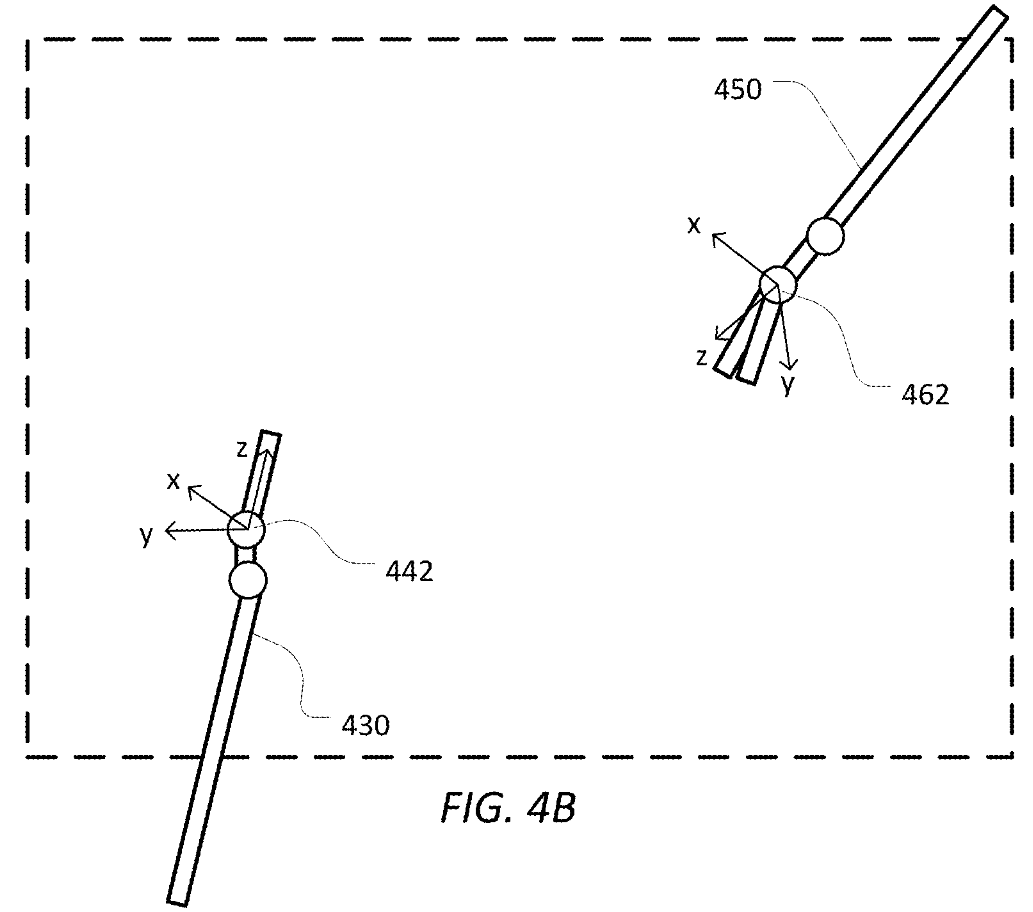
FIG. 4B is a simplified diagram of a view of an imaging device after an arm swap and/or port hop and before view restoration according to some embodiments.

FIG. 4B is a simplified diagram of a view of the imaging device after an arm swap and/or port hop and before view restoration according to some embodiments. As shown in the examples of FIG. 4B, instrument 410 has been replaced with the imaging device (e.g., by arm swapping the imaging device to the repositionable arm to which instrument 410 was mounted and/or removing instrument 410 from the workspace and port hopping the imaging device to the port previously used by instrument 410). Additionally, even though instruments 430 and 450 are depicted as being fully visible in FIG. 4B, some or all of each of the instruments may be occluded by each other, objects in the workspace (e.g., anatomy), and/or the like.

A comparison of FIGS. 4A and 4B shows that the view of the imaging device of FIG. 4A before the arm swap and/or port hop differs significantly from the view of the imaging device of FIG. 4B after the arm swap and/or port hop. The differences may be noted by observing that coordinate frame 442 of instrument 430 after the arm swap and/or port hop has a significantly different position and orientation than coordinate frame 440 of instrument 430 before the arm swap and/or port hop. Similarly, coordinate frame 462 of instrument 450 after the arm swap and/or port hop has a significantly different position and orientation than coordinate frame 460 of instrument 450 before the arm swap and/or port hop. In some cases, the differences in positions and/or orientations may make it difficult for an operator to quickly recognize that FIG. 4B shows a view of the same instruments 430 and 450. Similar to coordinate frames 420, 440, and/or 460, coordinate frames 442 and/or 462 may be mapped to a world coordinate frame and/or an imaging coordinate frame of the imaging device using one or more kinematic models.

Figures 4C, 5:
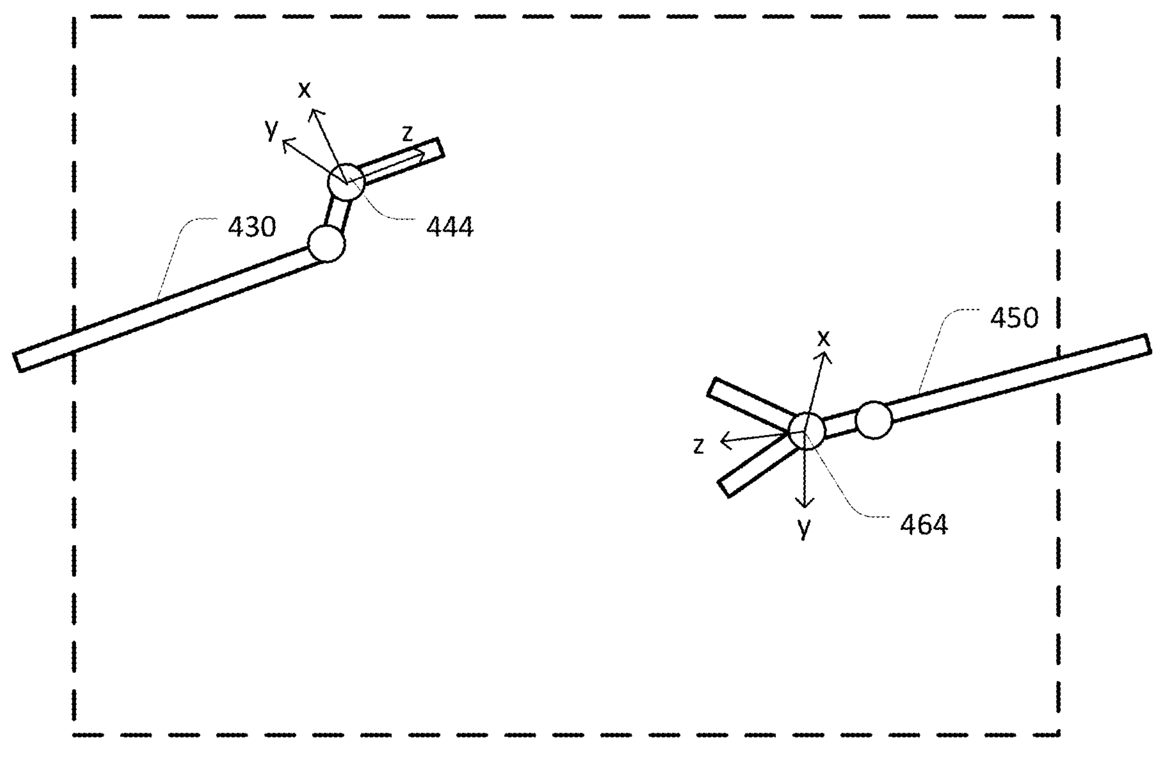
FIG. 4C is a simplified diagram of a view of an imaging device after an arm swap and/or port hop and after view restoration according to some embodiments.
FIG. 5 is a simplified diagram of a method of determining a view of an imaging device according to some embodiments.

FIG. 4C is a simplified diagram of a view of the imaging device after an arm swap and/or port hop and after view restoration according to some embodiments. As shown in the examples of FIG. 4C, the imaging device has been moved so as to restore the view of instruments 430 and 450 as well as the surrounding workspace. Additionally, even though instruments 430 and 450 are depicted as being fully visible in FIG. 4C, some or all of each of the instruments may be occluded by each other, objects in the workspace (e.g., anatomy), and/or the like.

A comparison of FIGS. 4A and 4C shows that the view of the imaging device of FIG. 4A before the arm swap and/or port hop differs somewhat from the view of the imaging device of FIG. 4C after the arm swap and/or port hop, but much less so than in the view of FIG. 4B. The differences may be noted by observing that coordinate frame 444 of instrument 430 after the arm swap and/or port hop and view restoration is much closer to the position and orientation of coordinate frame 440 of instrument 430 before the arm swap and/or port hop than that of coordinate frame 442. Similarly, coordinate frame 464 of instrument 450 after the arm swap and/or port hop and view restoration is much closer to the position and orientation of coordinate frame 460 of instrument 450 before the arm swap and/or port hop than that of coordinate frame 462. Similar to coordinate frames 420, 440, and/or 460, coordinate frames 444 and/or 446 may be mapped to a world coordinate frame and/or an imaging coordinate frame of the imaging device using one or more kinematic models.

However, because the imaging device after the arm swap and/or port hop has had its view restored so that the views of FIG. 4A and FIG. 4C are similar enough so as to aid an operator in being able to use instruments 430 and/or 450 after the arm swap and/or port hop.

Referring back to FIG. 3, at a process 310, kinematic and/or imaging information prior to an imaging device arm swap and/or port hop is recorded. The recorded kinematic and/or imaging information is used to determine a view of a workspace and/or one or more instruments in the workspace prior to the arm swap and/or port hop. The recorded information and the corresponding view so that they may be used to determine a desired imaging device position and orientation after the arm swap and/or port hop. In the embodiments of FIG. 4A, the recoded kinematic and/or imaging information may include information about the imaging coordinate frame, coordinate frames 420, 440, and/or 460, the kinematics used to determine these coordinate frames, and/or the like. Further examples of process 310 are described in further detail below.

At a process 320, the arm swap and/or the port hop of the imaging device is detected. In some examples, the arm swap may be automatically detected by observing the dismounting of the imaging device from a first repositionable arm and the subsequent mounting of the imaging device to a second repositionable arm. In some examples, one or more sensors, buttons, switches, electrical connections, magnetic detections, and/or the like may be used to determine whether the imaging device is dismounted and/or mounted to a respective repositionable arm. In some examples, the port hop may be automatically detected by observing the dismounting of the imaging device and/or a repositionable arm from a first port and the subsequent mounting of the imaging device and/or the repositionable arm to a second port. In some examples, one or more sensors, buttons, switches, electrical connections, magnetic detections, and/or the like may be used to determine whether the imaging device and/or the repositionable arm is dismounted and/or mounted to a respective port. In some examples, the arm swap and/or the port hop may be indicated by an operator by the press of a button, a voice command, a user interface command, and/or the like. In some examples, both a port hop and an arm swap may occur together (e.g., the imaging device is moved between repositionable arms and between workspace ports). In some examples, the arm swap and/or the port hop may include replacing a first imaging device with a second imaging device.

At a process 330, a desired position and orientation of the imaging device after the arm swap and/or the port hop is determined. In some examples, the desired position and/or orientation are determined so that the view of the imaging device after the arm swap and/or the port hop is as similar as possible to the view of the imaging device before the arm swap and/or the port hop as determined during process 310. In the embodiments of FIGS. 4A and 4C, the desired position and orientation of the imaging device may be determined so as reduce and/or minimize differences between coordinate frames 440 and 470 relative to the imaging device and/or coordinated frames 444 and 464 relative to the imaging device before and after the arm swap and/or port hop and view restoration, and/or the like. Examples of process 330 are described in further detail below.

At a process 340, the imaging device is moved to the desired position and orientation. In some examples, before the move is performed a motion plan for the imaging device is determined and then the imaging device is moved according to the motion plan. In some examples, the motion plan includes movement that reduces the risk of collisions between repositionable arms, between the imaging device and other instruments in the workspace, between the imaging device and objects and/or no-fly zones in the workspace, and/or the like. In some examples, the movement of the imaging device may be performed using one or more actuators of the repositionable arm to which the imaging device is mounted after the arm swap and/or port hop. In some examples, the actuators may be controlled using one or signals including one or more currents, one or more voltages, one or more pulse-width modulated signals, and/or the like. In some examples, one or more kinematic models, one or more Jacobians, and/or the like of the repositionable arm and/or the imaging device may be used in planning of the motion plan and/or in performing the movement of the repositionable arm and/or the imaging device. Examples of process 340 are described in further detail below.

FIG. 5 is a simplified diagram of a method 500 of determining a view of an imaging device according to some embodiments. One or more of the processes 510-540 of method 500 may be implemented, at least in part, in the form of executable code stored on non-transitory, tangible, machine-readable media that when run by one or more processors (e.g., the processor 140 in control unit 130) may cause the one or more processors to perform one or more of the processes 510-540. In some embodiments, portions of method 500 may be performed by a module, such as imaging control module 160. In some embodiments, method 500 may be performed as part of process 310. In some embodiments, method 500 determines a view of an imaging device based on information primarily associated with the imaging device. In some embodiments, method 500 may be used when fewer than two instruments are available on which to base the view of the imaging device.

At a process 510, a direction of view is determined based on imaging device information. In some examples, the direction of view may correspond to a direction between the imaging device and a center point of an image captured by the imaging device. In some examples, the direction of view corresponds to a z-axis of an imaging device coordinate frame of the imaging device. In some examples, the direction of view may be determined based on an inverse of one or more kinematic models of the imaging device and/or the repositionable arm to which the imaging device is mounted. In some examples, the direction of view may be determined in a world coordinate system, such as the world coordinate system described with respect to FIG. 4A. In some examples, the direction of view may correspond to a direction distally along an imaging axis of the imaging device, such as longitudinal axis 225 of imaging apparatus 220.

At a process 520, a view up direction is determined based on the imaging device information. In some examples, the view up direction corresponds to an upward direction in images captured by the imaging device. In some examples, the view up direction corresponds to a y-axis of the imaging device coordinate frame of the imaging device. In some examples, the view up direction may be determined based on the inverse of the one or more kinematic models of the imaging device and/or the repositionable arm to which the imaging device is mounted. In some examples, the view up direction may be determined in the world coordinate system. In some examples, the view up direction may correspond to a component of a direction opposite of gravity in the world coordinate frame (e.g., the z-axis of the world coordinate frame) that is orthogonal to the direction of view. In some examples, use of the direction of gravity to determine the view up direction may be preferable when the workspace is oriented with at least a vertical direction corresponding to up in the physical 3D world.

At a process 530, a depth of a point of interest from the imaging device is determined. In some examples, the point of interest corresponds to approximately a center of images captured by the imaging device. In some examples, the depth of the point of interest from the imaging device may be determined using a ranging sensor incorporated into the imaging device. In some examples, when the imaging device is stereoscopic, the depth of the point of interest from the imaging device may be determined based on pixel similarities and/or a disparity map between the left and right stereoscopic images captured by the imaging device. In some examples, the depth of the point of interest from the imaging device corresponds to a distance (e.g., a Euclidean) distance between the imaging device and the point of interest.

At a process 540, a position of a center of view of the imaging device is determined. The center of view may be determined by projecting from the imaging device along the direction of view as determined during process 510 a distance corresponding the depth of the point of interest from the imaging device as determined during process 530. In some examples, the center of view may be determined in the world coordinate frame.

Figure 6:
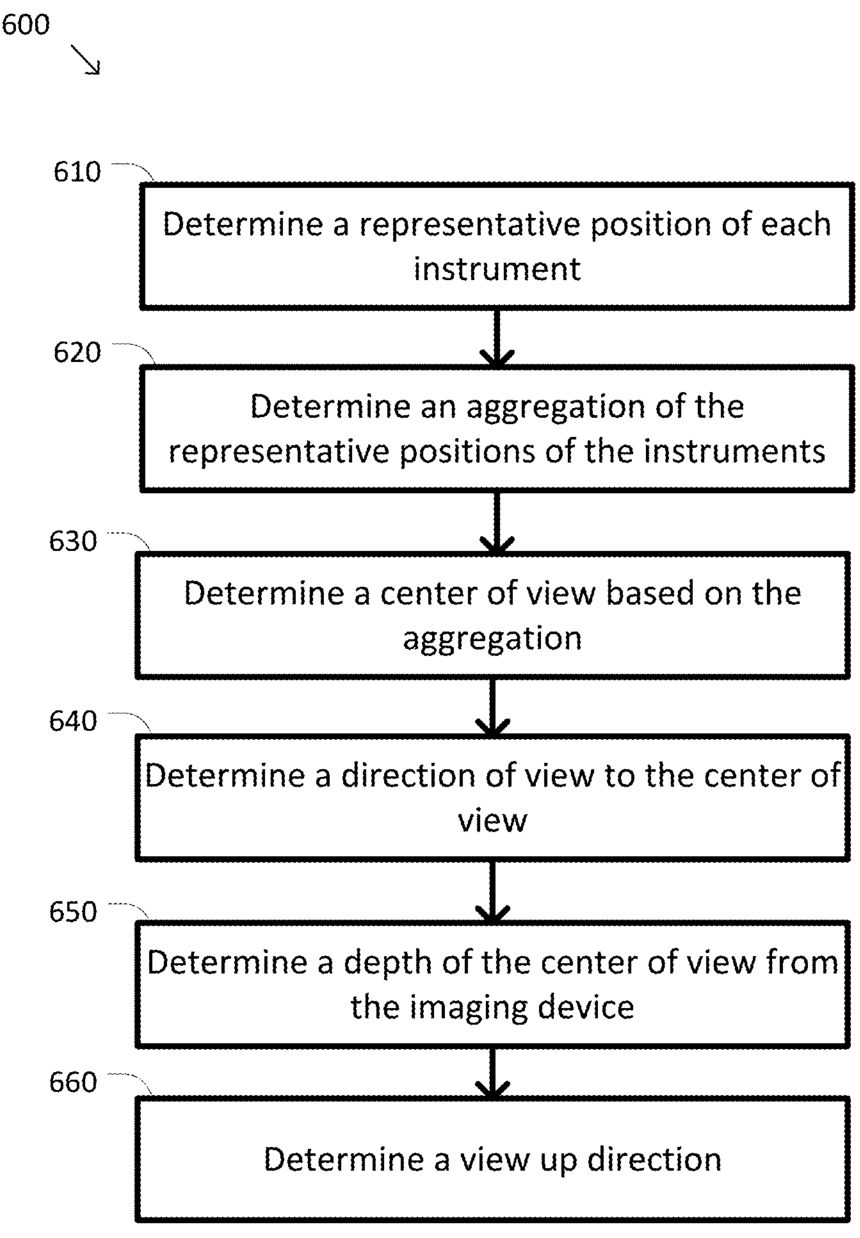
FIG. 6 is a simplified diagram of another method of determining a view of an imaging device according to some embodiments.

FIG. 6 is a simplified diagram of another method 600 of determining a view of an imaging device according to some embodiments. One or more of the processes 610-660 of method 600 may be implemented, at least in part, in the form of executable code stored on non-transitory, tangible, machine-readable media that when run by one or more processors (e.g., the processor 140 in control unit 130) may cause the one or more processors to perform one or more of the processes 610-660. In some embodiments, portions of method 600 may be performed by a module, such as imaging control module 160. In some embodiments, method 600 may be performed as part of process 310. In some embodiments, method 600 determines a view of an imaging device based on information primarily associated with a plurality of instruments that are within and/or near a field of view of the imaging device. In some examples, the plurality of imaging devices do not have to be visible in images captured by the imaging device.

According to some embodiments, the plurality of instruments to be considered by method 600 may be selected according to numerous strategies. In some examples, the plurality of instruments may include all of the instruments in the workspace other than the imaging device. In some examples, the plurality of instruments may include other imaging devices. In some examples, the plurality of instruments may include all of the instruments in the workspace except for imaging devices. In some examples, the plurality of instruments may include each of the instruments within the field of view (even if not visible) of the imaging device. In some examples, the instruments within the field of view may be determined based on one or more kinematic models of the plurality of instruments and/or the repositionable arms to which they are mounted, one or more kinematic models of the imaging device and/or the repositionable arm to which the imaging device is mounted, a width of view of the imaging device, and/or the like. In some examples, the field of view may be limited to regions closer than a maximum viewing depth to the imaging device and/or regions farther from the imaging device than a minimum viewing depth. In some examples, the plurality of instruments may include only those instruments designated as active by a computer-assisted device and/or an operator. In some examples, the plurality of instruments may include only those instruments designated as relevant to view determination by the operator.

At a process 610, a representative position of each of the plurality of instruments is determined. In some examples, the representative position of each of the plurality of instruments relative to the imaging device may be determined using one or more kinematic models of each of the instruments and/or the repositionable arms to which each of the plurality of instruments is mounted, such as is described with respect to FIGS. 4A-4C and Equation 1. In some examples, the representative position for an instrument may correspond representative point on an end effector of the instrument. In some examples, the presentative position for an instrument may correspond to an origin of a coordinate frame of the end effector of the instrument, such as the origin of coordinate frames 420, 440, 460, 444, and/or 464 in the examples of FIGS. 4A and 4C. In some examples, each of the representative positions may be represented by a bounding volume of a corresponding end effector. In some examples, the bounding volume may be a bounding sphere, a bounding rectangular shape, and/or a more complex shape that better approximates the shape of the corresponding end effector. In some examples, each of the representative positions may correspond to a centroid of the respective bounding volume.

At a process 620, an aggregation of the representative positions of the instruments is determined. In some examples, the aggregation may include determining a centroid of the representative positions, a centroid of the bounding volumes, and/or the like. In some examples, the aggregation may include a union of the bounding volumes, a circumscribing sphere that contains each of the representative positions and/or bounding volumes, and/or the like.

At a process 630, a center of view is determined based on the aggregation. In some examples, center of view may be the aggregation of the representative positions, a centroid of the aggregated bounding volumes, a centroid of the circumscribing sphere, and/or the like.

At a process 640, a direction of view to the center of view is determined. The direction of view is determined based on the direction from the imaging device to the center of view.

At a process 650, a depth of the center of view from the imaging device is determined. In some examples, the depth may be determined based on a distance (e.g., a Euclidean distance) from the imaging device to the center of view. In some examples, the depth may be determined by determining a viewing distance so that the view of the imaging device contains the aggregation of the bounding volumes determined during process 620 so that each of the representative positions and/or each of the bounding volumes are contained within the view of the imaging device.

At a process 660, a view up direction is determined. In some examples, the view up direction may be determined using a process similar to process 520.

According to some embodiments consistent with methods 300, 500, and/or 600, the combination of the direction of view, the view up direction, the depth of the point of interest/center of view from the imaging device, and the position of the center of view collectively determine the view for the imaging device. In some examples, when this view corresponds to the view of the imaging device before the arm swap and/or port hop, one goal will be to position and orient the imaging device after the arm swap and/or port hop so that the view of the imaging device after the arm swap and/or port hop is as close as practicable to the view of the imaging device before the arm swap and/or port hop.

Figure 7:
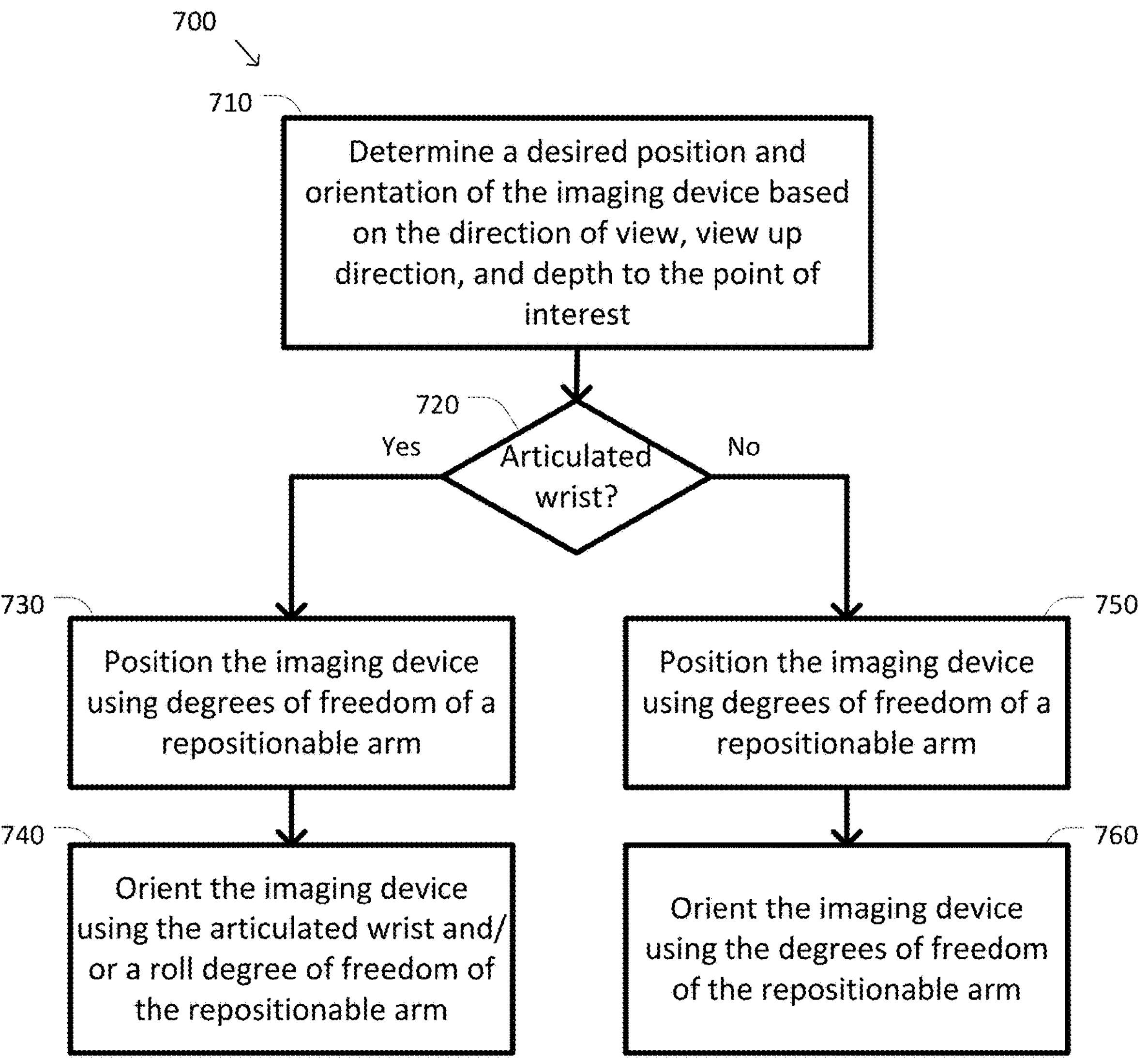
FIG. 7 is a simplified diagram of a method of moving an imaging device to obtain a desired view according to some embodiments.

FIG. 7 is a simplified diagram of a method 700 of moving an imaging device to obtain a desired view according to some embodiments. One or more of the processes 710-760 of method 700 may be implemented, at least in part, in the form of executable code stored on non-transitory, tangible, machine-readable media that when run by one or more processors (e.g., the processor 140 in control unit 130) may cause the one or more processors to perform one or more of the processes 710-760. In some embodiments, portions of method 700 may be performed by a module, such as imaging control module 160. In some embodiments, method 700 may be performed as part of processes 330 and/or 340. In some embodiments, method 700 moves the imaging device to obtain the desired view based on features of the imaging device and/or degrees of freedom by which the imaging device may be manipulated.

At a process 710, a desired position and orientation of the imaging device is determined based on the direction of view, the view up direction, and the depth to the point of interest/center of view from the imaging device, such as is determined by process 310, method 500, and/or method 600. The desired position of the imaging device corresponds to a point determined by projecting backward along the direction of view from the point of interest/center of view a distance corresponding to the depth of the point of interest/center of view from the imaging device. The desired orientation of the imaging device corresponds to aligning the imaging device with the direction of view and rolling the imaging device so that images captured by the imaging device are oriented consistent with the view up direction.

In some embodiments, when it is not possible to position the imaging device at the desired position and/or orient the imaging device consistent with the desired orientation, such as due to the imaging device and/or the repositionable arm to which the imaging device is mounted lacking sufficient degrees of freedom, the goals of obtaining the desired position and the desired orientation are balanced. In some examples, a tradeoff that balances distances between an actual center of view and the desired center of view (e.g., a Euclidean distance) and distances between an actual view up direction and the desired view up direction (e.g., an angular difference between the view up directions or a dot product of direction vectors for the view up directions) may be used to determine the desired position and orientation of the imaging device. In some examples the tradeoff may include minimizing a weighted sum of the distances. In some examples, the tradeoff may further balance the visibility of each of the instruments so that each of the instruments visible to the imaging device before the arm swap and/or port hop are visible to the imaging device after the arm swap and/or port hop and/or each of the instruments not visible to the imaging device before the arm swap and/or port hop are not visible to the imaging device after the arm swap and/or port hop.

At a process 720, it is determined whether the imaging device has an articulated wrist. In some examples, whether the imaging device has an articulated wrist may be determined based on a model and/or a type of the imaging device. In some examples, the model and/or type of the imaging device may be determined when the imaging device is mounted, such as by reading this information from a memory included in the imaging device. When the imaging device includes an articulated wrist, the imaging device is positioned and oriented beginning with a process 730. When the imaging device does not include an articulated wrist, the imaging device is positioned and oriented beginning with a process 750.

At the process 730, the imaging device is positioned using the degrees of freedom of the repositionable arm to which the imaging device is mounted. In some examples, the degrees of freedom include one or more of a pitch degree of freedom (e.g., about a remote center of motion, such as remote center of motion 250), a yaw degree of freedom (e.g., about the remote center of motion), an insertion degree of freedom (e.g., along an insertion axis, such as longitudinal axis 215), and/or the like.

At a process 740, the imaging device is oriented using the articulated wrist and/or a roll degree of freedom of the repositionable arm. In some examples, the roll degree of freedom corresponds to rotation of the imaging device about the insertion axis. In some examples, the articulated wrist may include one or more degrees of freedom including a pitch degree of freedom and/or a yaw degree of freedom, such as is consistent with the discussion of articulated wrist 230. In some examples, the articulation and/or anticipated articulation of the articulated wrist may be compensated for when the imaging device is positioned during process 730.

Once the imaging device is positioned and oriented, method 700 ends.

At the process 750, the imaging device is positioned using the degrees of freedom of the repositionable arm to which the imaging device is mounted. In some examples, the degrees of freedom include one or more of the pitch degree of freedom, the yaw degree of freedom, the insertion degree of freedom and/or the like described with respect to process 730.

At a process 760, the imaging device is oriented using the degrees of freedom of the repositionable arm. In some examples, the degrees of freedom include one or more of the roll degree of freedom, the pitch degree of freedom, the yaw degree of freedom, and/or the like of the repositionable arm.

Once the imaging device is positioned and oriented, method 700 ends.

As discussed above and further emphasized here, FIG. 7 is merely an example which should not unduly limit the scope of the claims. One of ordinary skill in the art would recognize many variations, alternatives, and modifications. According to some embodiments, the orders in which one or more of processes 730-760 is performed may be different than the order implied by FIG. 7. In some examples, process 740 may be performed before process 730. In some examples, processes 730 and 740 may be performed concurrently. In some examples, process 760 may be performed before process 750. In some examples, processes 750 and 760 may be performed concurrently. In some examples, movement of the imaging device along the insertion degree of freedom of the repositionable arm may be performed last.

According to some embodiments, movement along the insertion degree of freedom may not be performed automatically. In some examples, the roll, pitch, and/or yaw of the imaging device may be adjusted during processes 730-760 with the imaging device fully or partially retracted along its insertion degree of freedom with insertion of the imaging device along the insertion degree of freedom performed manually by the operator after method 700 completes. In some examples, the manual insertion of the imaging device may be performed by placing the imaging device and/or the repositionable arm in a clutched mode where manual articulation along the insertion degree of freedom is permitted. In some examples, insertion of the imaging device along the insertion degree of freedom may be performed via teleoperative control by the operator.

According to some embodiments, when the imaging device includes an angled shaft, process 710 may be adapted to consider both possible orientations of the bend in the shaft when selecting the desired position and orientation of the imaging device. The first orientation corresponds to the bend in the shaft being oriented in a first direction and the second orientation corresponds to the bend in the shaft being oriented in a flipped second direction where the roll orientation of the shaft of the imaging device is rotated 180 degrees. In some examples, selection of the second orientation may further include inverting images captured by the imaging device and, when the imaging device is stereoscopic, swapping the left and right images.

Figure 8:
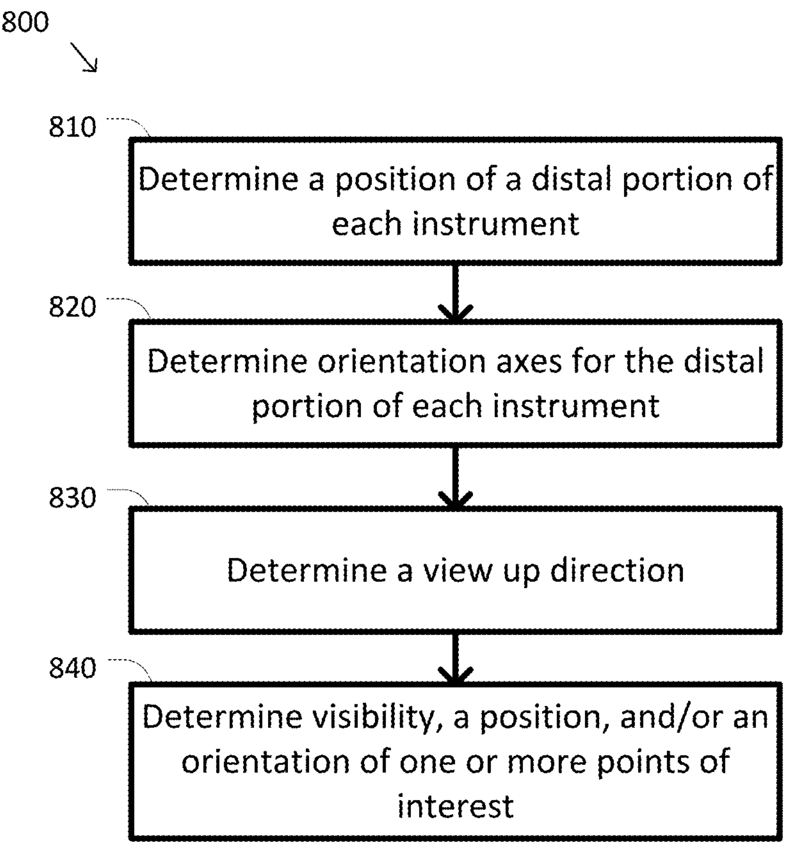
FIG. 8 is simplified diagram of a method of determining aspects of interest from a view according to some embodiments.

FIG. 8 is simplified diagram of a method 800 of determining aspects of interest from a view according to some embodiments. One or more of the processes 810-840 of method 800 may be implemented, at least in part, in the form of executable code stored on non-transitory, tangible, machine-readable media that when run by one or more processors (e.g., the processor 140 in control unit 130) may cause the one or more processors to perform one or more of the processes 810-840. In some embodiments, portions of method 800 may be performed by a module, such as imaging control module 160. In some embodiments, method 800 may be performed as part of process 310. In some embodiments, method 800 determines a view of an imaging device based on information associated with both the imaging device and one or more instruments that are within and/or near a field of view of the imaging device. In some examples, the instruments do not have to be visible in images captured by the imaging device. In some embodiments, one or more of processes 830 and/or 840 is optional and may be omitted.

According to some embodiments, the selection of the one or more instruments considered by method 800 may be selected according to any of the strategies described for the selection of the plurality of instruments to be considered by method 600.

At a process 810, a position of a distal portion of each instrument is determined. In some examples, the distal portion of each instrument may correspond to a representative point on the respective instrument (e.g., a distal tip of the end effector, a centroid of the end effector, a pivot point between jaws of the end effector, and/or the like). In some examples, the position of the distal portion of each end effector may be mapped to a world coordinate frame using an inverse of one or more kinematic models of the respective instrument and a repositionable arm to which the respective instrument is mounted. In some examples, the position of the distal portion of each instrument may be additionally mapped to a viewing coordinate frame of the imaging device using one or more kinematic models of the imaging device and a repositionable arm to which the imaging device is mounted. In the examples of FIGS. 4A and 4B, the position of the distal portion of instruments 410, 430, and/or 450 may correspond to the origin of coordinate frame 420 for instrument 410, coordinate frames 440 and/or 470 for instrument 430, and/or coordinate frames 460 and/or 480 for instrument 450.

At a process 820, orientation axes for the distal portion of each instrument is determined. Each of the orientation axes of each of the one or more instruments may be determined using one or more kinematic models of each of the instruments and/or the repositionable arms to which each of the plurality of instruments is mounted, such as is described with respect to FIGS. 4A and 4B. In the examples of FIGS. 4A and 4B, the orientation axes of the distal portion of instruments 410, 430, and/or 450 may correspond to the x, y, and z axes of coordinate frame 420 for instrument 410, coordinate frames 440 and/or 470 for instrument 430, and/or coordinate frames 460 and/or 480 for instrument 450.

At an optional process 830, a view up direction is determined. In some examples, the view up direction may be determined using a process similar to processes 520 and/or 660.

At an optional process 840, a visibility, a position, and/or an orientation of one or more points of interest is determined. In some examples, the one or more points of interest may correspond with additional representative points on the one or more instruments and/or one or more points of interest in the workspace. In some examples, each of the one or more points of interest may correspond to a fiducial marker and/or other element detectable in images captured by the imaging and/or detectable by other sensing approaches (e.g., radio frequency, magnetic, and/or the like). In some examples, when a point of interest is associated with and/or is positioned at a known location on one of the one or more instruments, the one or more kinematic models of the instruments and/or the repositionable arm to which the instrument is mounted may be used to determine the position and/or the orientation of the point of interest. In some examples, the visibility of each of the one or more points of interest may be used to help characterize a view by which of the one or more points of interest are visible and which of the one or more points of interest are not visible.

Figure 9:
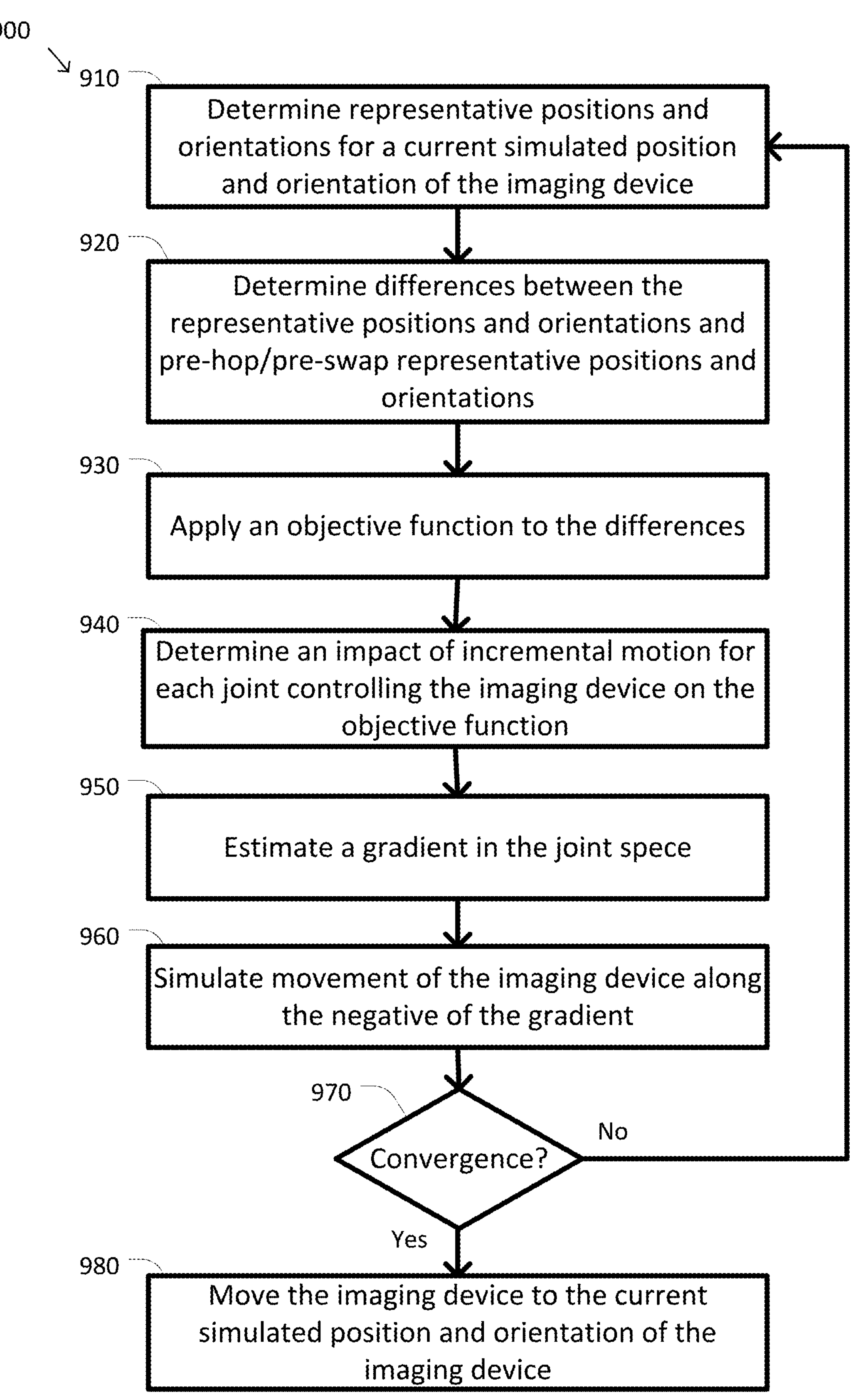
FIG. 9 is simplified diagram of a method of view restoration according to some embodiments.

FIG. 9 is simplified diagram of a method 900 of view restoration according to some embodiments. One or more of the processes 910-980 of method 900 may be implemented, at least in part, in the form of executable code stored on non-transitory, tangible, machine-readable media that when run by one or more processors (e.g., the processor 140 in control unit 130) may cause the one or more processors to perform one or more of the processes 910-980. In some embodiments, portions of method 900 may be performed by a module, such as imaging control module 160. In some embodiments, method 900 may be performed as part of processes 330 and 340. In some embodiments, method 900 determines a desired position and orientation of an imaging device after an arm swap and/or port hop using a gradient-descent style approach and then moves the imaging device to the desired position and orientation.

At a process 910, representative positions and orientations for a current simulated position and orientation of the imaging device are determined. In some examples, the representative positions and orientations may include a position of the distal portion of each of the instruments, the orientation axes of the distal portion of each of the instruments, the position of each of the one or more points of interest, the orientation of each of the one or more points of interest, and/or the like in the imaging device coordinate frame at the current simulated position and orientation of the imaging device. In some examples, the representative positions and orientations may include the view up direction of the imaging device when the imaging device is in the current simulated position and orientation. In some examples, the representative positions and orientations may include an indication of which of the one or more points of interest are visible and/or within the field of view of the imaging device when the imaging devices is in the current simulated position and orientation. In some examples, the representative positions and orientations may correspond to any of the positions and orientations determined by method 800 and may be determined using an approach consistent with method 800.

At a process 920, differences are determined between the representative positions and orientations and the same representative positions and orientations before the arm swap and/or port hop. In some examples, the differences between two corresponding representative positions may be determined using any suitable distance measure, such as the Euclidean distance. In some examples, the differences between two corresponding representative orientations (e.g., the directions of two corresponding orientation axes) may be determined based on an absolute angular difference between the orientations, a dot product of the two orientation axes, and/or the like. In some examples, the difference between the view up vector before the arm swap and/or port hop and the view up direction when the imaging device is in the current simulated position and orientation may be determined based on an angular difference between the two view up directions, a dot product of unit axes corresponding to the two view up directions, and/or the like. In some examples, the difference between two visibility values may be zero when the visibility is the same (both visible or both not visible) or one when visibility is different (one visible and the other not visible).

At a process 930, an objective function is applied to the differences determined during process 920. In some examples, the objective function may include computing a weighted sum of each of the differences. In some examples, each of the weights in the weighted sum may be selected based on which of the representative positions and orientations is considered more important in finding two views similar. In some examples, a weighting may be set to zero to ignore one of the representative positions and/or orientations in the view comparison. In some examples, one or more other objective functions may be used.

At a process 940, an impact of incremental motion for each joint controlling the imaging device on the objective function is determined. For each joint in the imaging device (e.g., each of the joints in an articulated wrist of the imaging device) and in the repositionable arm to which the imaging device is mounted, an incremental amount of motion for that joint is simulated. As the incremental motion of each joint is simulated, the change of the incremental motion on the view of the imaging device is determined by simulating the motion. Once the incremental motion of the imaging device is simulated, the differences in the representative positions and orientations relative to the imaging device due to the incremental motion are determined. The objective function is then applied to the differences (e.g., by repeating processes similar to processes 910-930).

At a process 950, a gradient in the joint space is determined by combining the impact of each of the incremental motions on the objective function as determined during process 940. In some examples, a numerical interpolating/extrapolating approach, such as the use of divided differences, may be used to combine the impact on the objective function of each of the incremental motions to determine the gradient.

At a process 960, movement of the imaging device along the negative of the gradient is simulated. In some examples, each of the joints controlling the imaging device is simulated to change its position proportional to that joint's coefficient in the gradient, but in a direction opposite to the gradient. In some examples, amount of simulated movement may also be scaled by a coefficient. In some examples, movement along the negative gradient tends to reduce the aggregated differences between the view of the imaging device before the arm swap and/or port hop and the view of the imaging device with each successive movement by process 960.

At a process 970, it is determined whether the objective function of the differences between the view of the imaging device before the arm swap and/or port hop and the view of the imaging device for the current simulated position and orientation of the imaging device is converged. In some examples, the objective function of the differences is converged when changes in the objective function of the differences between successive simulated movements by process 960 are below a threshold. In some examples, the objective function of the differences are converged when a magnitude of the gradient is below a threshold (e.g., a distance of the movement simulated by process 960 is below a threshold). When the objective function of the differences is not converged, processes 910-970 are repeated using the position and orientation of the imaging device after the simulated movement as the current simulated position and orientation of the imaging device. When the objective function of the differences is converged, the view of the imaging device is restored using a process 980.

At the process 980, the imaging device is moved to the current simulated position and orientation of the imaging device. In some examples, process 980 may be substantially similar to process 340 and/or method 700 with the current simulated position and orientation of the imaging device being the desired position and orientation of the imaging device.

As discussed above and further emphasized here, FIG. 9 is merely an example which should not unduly limit the scope of the claims. One of ordinary skill in the art would recognize many variations, alternatives, and modifications. According to some embodiments, method 900 may be terminated when convergence of the objective function of the differences is not detected after a threshold number of iterations. In some examples, the number of iterations may be determined using a counter incremented with each pass through the loop of processes 910-970. In some examples, when method 900 is terminated due to lack of convergence, an error or other indication to an operator may be made indicating that automated view restoration could not be completed. In some examples, when method 900 is terminated due to lack of convergence, view restoration may be performed manually by the operator.

According to some embodiments, method 900 may account for other practical considerations. In some examples, the incremental motions considered by process 940 or included via the gradient in process 950 and/or 960 may be limited due to range of motion limits of the joints controlling the imaging device, to perform collision avoidance, and/or the like. In some examples, a range of motion limit for a joint may be a physical range of motion limit and/or a software-defined range of motion limit defined before the physical range of motion limit is reached.

Some examples of control units, such as control unit 130 may include non-transitory, tangible, machine readable media that include executable code that when run by one or more processors (e.g., processor 140) may cause the one or more processors to perform the processes of methods 300, 500, 600, 700, 800, and/or 900. Some common forms of machine readable media that may include the processes of methods 300, 500, 600, 700, 800, and/or 900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
a first repositionable arm comprising a plurality of joints and a plurality of actuators, the plurality of actuators configured to cause movement of the first repositionable arm; and
a controller comprising one or more hardware processors, the controller communicatively coupled to the first repositionable arm;
wherein the controller is configured to:
determine whether an imaging device supported by the first repositionable arm comprises an articulable joint that couples an imaging apparatus to a shaft of the imaging device;
in response to a determination that the imaging device comprises the articulable joint:
command the plurality of actuators to move the plurality of joints and the articulable joint to position and orient a field of view of the imaging apparatus; and
in response to a determination that the imaging device does not comprise the articulable joint:
command the plurality of actuators to move the plurality of joints to position and orient the field of view of the imaging apparatus.

2. The computer-assisted device of claim 1, wherein to command the plurality of actuators to move the plurality of joints and the articulable joint to position and orient the field of view, the controller is configured to:
command the plurality of actuators to move the plurality of joints to position the imaging device and to move the articulable joint to orient the field of view.

3. The computer-assisted device of claim 1, wherein:
to command the plurality of actuators to move the plurality of joints and the articulable joint to position and orient the field of view, the controller is configured to: command the plurality of actuators to move the plurality of joints to position a distal portion of the imaging device at a first position and to move the articulable joint to orient the field of view in a first orientation; and
to command the plurality of actuators to move the plurality of joints to position and orient the field of view, the controller is configured to: command the plurality of actuators to move the plurality of joints to position the distal portion at the first position and to orient the field of view in the first orientation.

4. The computer-assisted device of claim 1, wherein to determine whether the imaging device comprises the articulable joint, the controller is configured to:
read a type of the imaging device stored in a memory of the imaging device.

5. The computer-assisted device of claim 1, wherein the controller is further configured to:
determine a first position based on a desired direction of view of the imaging apparatus, and a depth of a point of interest from the imaging apparatus, wherein the first position defines a position of a distal portion of the imaging device; and
determine a first orientation based on the desired direction of view and a desired view up direction, wherein the first orientation defines an orientation of the distal portion.

6. The computer-assisted device of claim 5, wherein to determine the first position, the controller is configured to:
project, from the point of interest, in a direction backward relative to the direction of view and for a distance corresponding to the depth of the point of interest.

7. The computer-assisted device of claim 5, wherein to orient the field of view in the first orientation, the controller is configured to:
align the imaging apparatus with the desired direction of view; and
roll the imaging apparatus so that images captured by the imaging apparatus are oriented consistently with the view up direction.

8. The computer-assisted device of claim 5, wherein:
the imaging device is introduced into a workspace using a first workspace port; and
the controller is further configured to determine the desired direction of view based on a direction defined by the imaging apparatus and a center point of a previous image captured by the imaging apparatus; and
the previous image was captured when:
the imaging device was previously supported by a second repositionable arm different from the first repositionable arm; or
the imaging device was previously introduced into the workspace using a second workspace port different from the first workspace port.

9. The computer-assisted device of claim 5, wherein:
the imaging device is introduced into a workspace using a first workspace port; and
the controller is further configured to determine the view up direction based on a previous view up direction of a previous image captured by the imaging apparatus; and
the previous image was captured when:
the imaging device was previously supported by a second repositionable arm different from the first repositionable arm; or
the imaging device was previously introduced into the workspace using a second workspace port different from the first workspace port.

10. The computer-assisted device of claim 5, wherein:
the imaging device is introduced into a workspace using a first workspace port; and
the controller is further configured to determine the depth of the point of interest based on a distance from the distal portion to the point of interest, the distance being when the imaging device was previously supported by a second repositionable arm different from the first repositionable arm, or when the imaging device was previously introduced into the workspace using a second workspace port different from the first workspace port.

11. The computer-assisted device of claim 5, wherein the controller is further configured to:
determine a representative point or a bounding volume for each of a plurality of instruments; and
determine the point of interest based on an aggregation of the representative points or an aggregation of the bounding volumes.

12. A method comprising:
determining, by a controller, whether an imaging device has an articulable joint that couples an imaging apparatus to a shaft of the imaging device, the imaging device being supported by a first repositionable arm, the first repositionable arm comprising a plurality of joints and a plurality of actuators configured to cause movement of the first repositionable arm and the imaging device;
on a condition that the imaging device comprises the articulable joint:
commanding, by the controller, the plurality of actuators to move the plurality of joints and the articulable joint to position and orient a field of view of the imaging apparatus; and
on a condition that the imaging device does not comprise the articulable joint:
commanding, by the controller, the plurality of actuators to move the plurality of joints to position and orient the field of view of the imaging apparatus.

13. The method of claim 12, wherein commanding the plurality of actuators to move the plurality of joints and the articulable joint to position and orient the field of view comprises:
commanding the plurality of actuators to move the plurality of joints to position the imaging device and to move the articulable joint to orient the field of view.

14. The method of claim 12, further comprising:
determining, by the controller, a first position based on a desired direction of view of the imaging apparatus and a depth of a point of interest from the imaging apparatus, wherein the first position defines a position of a distal portion of the imaging device; and
determining, by the controller, a first orientation based on the desired direction of view and a desired view up direction, wherein the first orientation defines an orientation of the distal portion.

15. The method of claim 14, wherein orienting the field of view in the first orientation comprises:
aligning the imaging apparatus with the desired direction of view; and
rolling the imaging apparatus so that images captured by the imaging apparatus are oriented consistent with the view up direction.

16. The method of claim 14, wherein the imaging device is introduced into a workspace using a first workspace port, the method further comprising:
determining, by the controller, the desired direction of view based on a direction defined by the imaging apparatus and a center point of an image captured by the imaging apparatus;
wherein the image was captured when:
the imaging device was previously supported by a second repositionable arm different from the first repositionable arm; or
the imaging device was previously introduced into the workspace using a second workspace port different from the first workspace port.

17. The method of claim 14, wherein the imaging device is introduced into a workspace using a first workspace port, the method further comprising:
determining, by the controller, the view up direction based on a previous view up direction of a previous image captured by the imaging apparatus; and
the previous image was captured when:
the imaging device was previously supported by a second repositionable arm different from the first repositionable arm; or
the imaging device was previously introduced into the workspace using a second workspace port different from the first workspace port.

18. The method of claim 14, wherein the imaging device is introduced into a workspace using a first workspace port, the method further comprising:
determining, by the controller, the depth of the point of interest based on a distance from the distal portion to the point of interest, the distance being when the imaging device was previously supported by a second repositionable arm different from the first repositionable arm; or, when the imaging device was previously introduced into the workspace using a second workspace port different from the first workspace port.

19. A non-transitory machine-readable medium comprising a plurality of machine-readable instructions which, when executed by one or more processors associated with a computer-assisted device, are adapted to cause the one or more processors to perform a method comprising:
determining whether an imaging device comprises an articulable joint that couples an imaging apparatus to a shaft of the imaging device, the imaging device being supported by a first repositionable arm, the first repositionable arm comprising a plurality of joints and a plurality of actuators configured to control movement of the first repositionable arm and the imaging device;
in response to determining that the imaging device comprises the articulable joint:
commanding the plurality of actuators to move the plurality of joints and the articulable joint to position and orient a field of view of the imaging apparatus; and in response to determining that the imaging device does not comprise the articulable joint:

commanding the plurality of actuators to move the plurality of joints to position and orient the field of view of the imaging apparatus.

20. The non-transitory machine-readable medium of claim 19, wherein:

commanding the plurality of actuators to move the plurality of joints and the articulable joint to position and orient the field of view comprises: commanding the plurality of actuators to move the plurality of joints to position a distal portion of the imaging device at a first position and to move the articulable joint to orient the field of view in a first orientation; and commanding the plurality of actuators to move the plurality of joints to position and orient the field of view comprises: commanding the plurality of actuators to move the plurality of joints to position the distal portion at the first position and to orient the field of view in the first orientation.

* * * * *